United States Patent
Trabucco

Patent Number: 6,166,286
Date of Patent: Dec. 26, 2000

[54] MESH PLUG KIT FOR THE INGUINAL BOX SURGICAL TECHNIQUE FOR HERNIOPLASTY

[75] Inventor: Ermanno Trabucco, Great Neck, N.Y.

[73] Assignee: Arcilius Consultadoria e Servicos Lda, Madeira, Portugal

[21] Appl. No.: 09/154,458

[22] Filed: Sep. 16, 1998

[51] Int. Cl.$^7$ ...................................... A61F 2/02
[52] U.S. Cl. ............................................. 623/11; 606/151
[58] Field of Search ........................ 623/11, 12; 606/151, 606/153, 154, 213, 215

[56] References Cited

U.S. PATENT DOCUMENTS

| | | |
|---|---|---|
| 2,671,444 | 3/1954 | Pease . |
| 4,769,038 | 9/1988 | Bendavid et al. . |
| 5,334,217 | 8/1994 | Das .......................................... 606/151 |
| 5,356,432 | 10/1994 | Rutkow et al. ............................ 623/11 |
| 5,425,740 | 6/1995 | Hutchinson, Jr. ........................ 606/157 |
| 5,697,978 | 12/1997 | Sgro .......................................... 623/12 |
| 5,716,409 | 2/1998 | Debbas . |
| 5,725,577 | 3/1998 | Saxon ........................................ 623/11 |
| 5,741,297 | 4/1998 | Simon ...................................... 606/213 |
| 5,879,366 | 3/1999 | Shaw et al. .............................. 606/213 |

FOREIGN PATENT DOCUMENTS

| | | |
|---|---|---|
| 0 614 650 A2 | 2/1994 | European Pat. Off. . |
| 0 719 527 A1 | 12/1995 | European Pat. Off. . |
| WO 96/14805 | 5/1996 | WIPO . |

*Primary Examiner*—Michael J. Milano
*Attorney, Agent, or Firm*—Collard & Roe, P.C.

[57] ABSTRACT

A series of kits for an indirect inguinal hernia operation for both a male patient and a female patient. The kit for the male patient comprises two plugs and one mesh piece. The plugs and mesh are made from a polymer mesh and are pretreated so that they lay flat within the body after a hernia operation. These two plugs and mesh piece are sterilized and placed within a kit so that during an operation for hernia repair, a doctor has the necessary plugs precut and sterilized so that he can place these plugs within a patient's body. The hernia operation involves exposing an inguinal box that is 12 centimeters in length by 4.5 centimeters in width. The first of the two plugs has a circular shape with a diameter of 5 centimeters. The second of the two plugs has a circular shape with a diameter of 4 centimeters and a center hole with a slit cut from an edge leading to the center hole. The first mesh piece has a length of 10 centimeters and a width of 4.5 centimeters and also has a center hole with a slit cut from one edge leading to the center hole. The second plug and mesh piece have holes and slits so that they can fit around a spermatic cord in a patient's body. In addition, there is also a kit for a female patient. This kit comprises the first plug and a second mesh piece that is tear drop-shape with a length of 10 centimeters, and a width of 4.5 centimeters. Since a female patient does not have a spermatic cord, the plug and mesh piece in this kit do not have holes or slits for a spermatic cord.

14 Claims, 5 Drawing Sheets

MESH PLUG KIT FOR THE INGUINAL BOX SURGICAL TECHNIQUE FOR HERNIOPLASTY

BACKGROUND OF THE INVENTION

1. Field of the Invention

The invention relates to a plurality of kits for use in an indirect inguinal hernia operation. The operation consists of exposing a 12 centimeter by 4.5 centimeter "Inguinal Box" for the insertion of mesh-plugs. These kits are comprised a series of plugs and mesh pieces of various shapes and sizes with one of the plugs and one of the mesh pieces having a hole in the center to fit around the spermatic cord.

2. Description of the Prior Art

Many inguinal hernia plugs are known in the prior art. For example, U.S. Pat. No. 5,716,409 to Debbas discloses a reinforcement sheet for use in surgery that includes an opening to receive a spermatic cord and a passageway designed to allow the opening to fit around the spermatic cord.

U.S. Pat. No. 4,769,038 to Bendavid et al. discloses a plug for the repair of a femoral hernia. The plug or prosthesis has multiple layers or panels and fits around the spermatic cord.

U.S. Pat. No. 2,671,444 to Pease discloses a non metallic mesh surgical insert for hernia repair. The non metallic mesh surgical insert is preferably made from a polyethylene mesh known under the trade mark Alathon.

PCT Application No. WO 96/14805 to Valenti discloses a double layer prosthesis that is applied to a patient with an inguinal hernia.

European Patent No. 0719527A1 to Sgro discloses a dual layer prosthesis for an indirect inguinal hernia. The first layer is a solid sheet while the second layer has a center hole and a strip cut towards the center hole.

European Patent No. 0614650 to Rutkow discloses an implantable prosthesis that has a conical mesh plug having a pleated surface which conforms to the contours of the defect being repaired. Mesh filler material positioned on the plug stiffens the implant when it is compared to the defect.

Unlike the prior art, the present invention is a set of plugs and hernia mesh pieces for a particular surgical technique. This technique involves exposing an approximately 12 centimeter by 4.5 centimeter box or opening in a patient. One of two kits can be used with this surgical technique with one kit for male patients and another kit for female patients. Each kit comprises a series of pre sterilized and pre tensioned mesh plugs that are cut to fit inside this box.

SUMMARY OF THE INVENTION

Indirect inguinal hernia operations have been performed on patients for many years. The operation involves exposing an approximately 12 centimeter by 4.5 centimeter inguinal box that includes a lateral box and a medial box. The lateral box extends from a deep inguinal ring to a superior iliac spine and averages 7 centimeters in length. This lateral box is a virtual space that contains a loose vascular thin areolar tissue laying between an internal oblique muscle and an external oblique aponeurosis. The medial box extends from the deep inguinal ring to the pubic tubercle. This box extends 6 centimeters in length and includes 1 centimeter of the pubic tubercle. A superficial inguinal ring is an opening in the roof of the medial box, while a deep inguinal ring is an opening in its floor.

Using the kit of the invention, a surgeon has the option to insert a series of plugs and meshes found in a kit. One of two kits can be used with this surgical technique with one kit for male patients and another kit for female patients. Each kit is comprised of at least one plug and at least one mesh, selected from a total of two plugs and two meshes. All of these pieces are presterilized and precut so that during surgery, a surgeon can open the sterile package and apply the plugs and meshes to the patient without the need to individually cut the plugs or meshes or to separately sterilize them.

The plugs and meshes are made from a polypropylene monofilament that is woven into a mesh, stretched, and then treated with hot vapors to diminish its memory. This mesh is next cut into the desired shapes with a laser or a hot knife to burn the ends of the mesh so as to keep the monofilament mesh from fraying.

A first kit is used for repairing indirect inguinal hernias in male patients. This kit comprises two plugs and one mesh piece. The first plug is a round mesh patch that is at least 2.5 centimeters but preferably 5 centimeters in diameter. The second plug is a round mesh patch that is at least 2.5 centimeters but preferably 4 centimeters in diameter with a central hole of 1 centimeter in diameter and a lateral slit. The central hole and lateral slit allow this second plug to fit around a spermatic cord within a patient's body.

The hernia mesh piece is tear-drop-shaped having a right edge, a left edge, a top edge and a bottom edge. In addition, this mesh piece has a circular hole with a diameter of 1.2 centimeters. The center of this hole is 1.5 centimeters up from the bottom edge, 3 centimeters in from the top edge, 4 centimeters in from the right edge and 6 centimeters in from the rounded left edge. Furthermore, a cutaway strip is placed into the plug so that a spermatic cord can fit inside the center hole.

During an operation on a male patient, one of the plugs is inserted into the deep inguinal ring below the tranversalis fascia. A surgeon has the option of using one of the two plugs depending on his preference. The second plug is preferred because it can fit around a patient's spermatic cord thereby limiting the movement of the plug within the patient's body. In addition, these plugs and mesh pieces are cut with particular dimensions to fit snug inside an inguinal box. Therefore, the walls of the inguinal box hold the mesh pieces within the box and keep them from migrating. Since there is little migration of these plugs within the body, there is less chance of seromas, deformities, and incomplete fibrous infiltration.

The second kit comprises the first plug plus a second hernia mesh piece that is tear-drop-shaped piece having a right edge, a left edge, a top edge, and a bottom edge. This first mesh piece has a width of 4 centimeters along the right edge that gradually increases to a width of 4.5 centimeters at its widest point. The piece then tapers down to a rounded left edge. In addition, the piece has a length of 10 centimeters.

This second kit can be used to treat female patients. During an operation, the first plug can be placed within the deep inguinal ring, underneath the transversalis fascia. Next the hernia mesh piece is placed within the superficial inguinal ring, inside inguinal box but over the transversalis fascia and the first plug.

One object of the invention is to provide a kit for male patients having the first and second plugs and the first hernia mesh piece.

Another object of the invention is to provide a kit for female patients having the first plug and the second hernia mesh piece.

Another object of the invention is to provide a plug for an indirect inguinal hernia that lays flat within the body, thus avoiding complications during surgery such as seromas, deformities and incomplete fibrous infiltration.

Another object of the invention is to provide a plug or piece for an indirect inguinal hernia that can be applied into a body without the use of sutures or staples.

It is a further object of the invention to provide a series of plugs and meshes that fit within an inguinal box that extends roughly 12 centimeters from the superior iliac spine to the pubic tubercle and roughly 4.5 centimeters from the aponeurotic attachment of the external oblique on the anterior rectus sheath to the reflection of the inguinal ligament.

BRIEF DESCRIPTION OF THE DRAWINGS

Other objects and features of the present invention will become apparent from the following detailed description considered in connection with the accompanying drawings which disclose two embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF THE PREFERRED EMBODIMENT

Figure 1A:
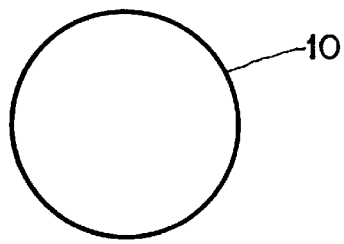
FIG. 1A discloses a front view of the first hernial plug.
Figure 1B:
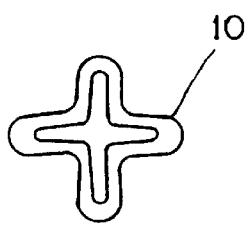
FIG. 1B discloses a front view of the first hernial plug that is pinched.

Referring to FIG. 1A there is shown a first plug 10 that is a single round circular plug. This plug has a diameter of 5 centimeters. As shown in FIG. 1B it can be pinched together so that it can be inserted into a small opening within the body.

Figure 1C:
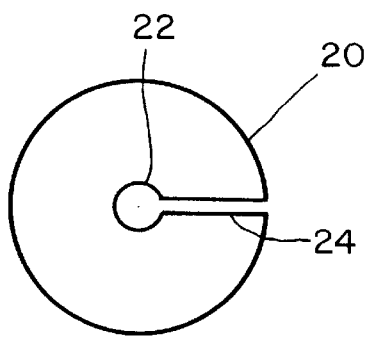
FIG. 1C discloses a front view of the second hernial plug having a center cut out designed to fit around the spermatic cord.

FIG. 1C shows a second plug 20 that has a center hole 22, and a strip 24 cut in from its edge to the center hole. This plug is 4 centimeters in diameter. Center hole 22 and strip 24 are designed to allow second plug 20 to fit around a spermatic cord. During an operation, second plug 20 can be opened along strip 24 to allow center hole 22 to fit around a spermatic cord within a patient's body.

Figure 1E:
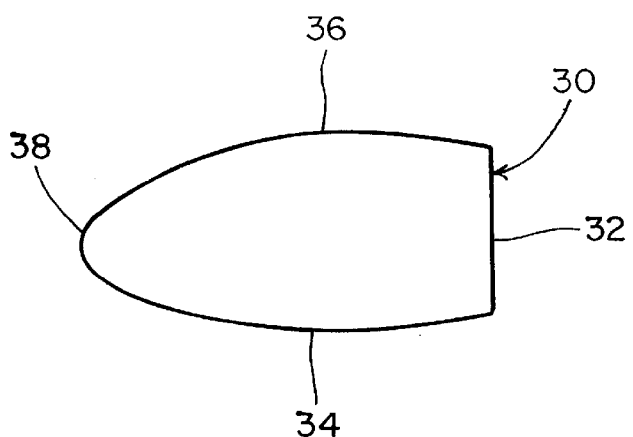
FIG. 1E is a front view of the second hernial mesh piece
Figure 1D:
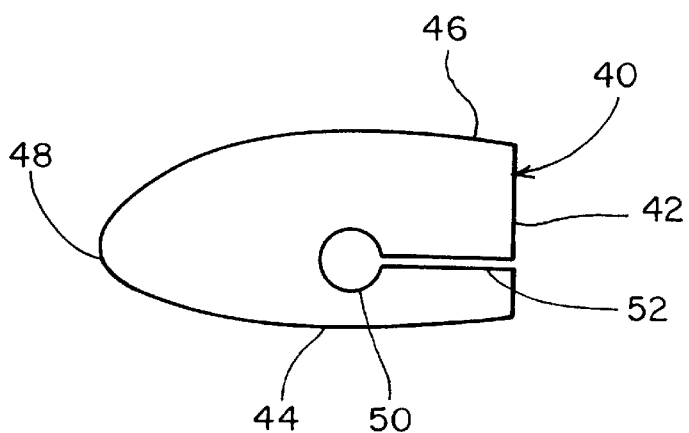
FIG. 1D discloses a front view of the first hernia mesh piece having a center cut designed to fit around the spermatic cord.

FIG. 1D shows the first hernia mesh piece 40 in the kit wherein there is a right edge 42, a left edge 48, a bottom edge 44 and a top edge 46. A hole 50 has a center that is positioned 1.5 centimeters up from the bottom edge 44, and 3 centimeters down from the top edge. In addition, hole 50 is placed 4 centimeters in from right edge 32 and 6 centimeters in from left edge 48. Piece 40 also has strip 52 that extends from right edge 42 to hole 50. Strip 52 is placed 1.5 centimeters in from bottom edge 44 and 3 centimeters in from top edge 46. Like second plug 20, hole 50 and strip 52 on piece 40 are designed to allow piece 40 to fit around a spermatic cord.

FIG. 1E shows a second hernia mesh piece 30 that has a right edge 32, a left edge 38 a bottom edge 34 and a top edge 36. Mesh piece 30 is 4 centimeters wide along right edge 32, and 4.5 centimeters at its widest point. In addition, mesh piece 30 is 10 centimeters long extending from right edge 32 to left edge 38.

Both plugs 10 and 20 and meshes 30, and 40 are made from a polypropylene monofilament that is woven into a mesh, stretched, and then treated with hot vapors to diminish its memory. This mesh is cut into the above-mentioned dimensions with a laser or hot knife to burn the ends of the mesh so as to keep the monofilament mesh from fraying. Next, these two plugs 10 and 20 and meshes 30 and 40 are sterilized and placed in one of two kits. The first kit is designed for an indirect inguinal hernia operation on a male patient. In this type operation, the first, and second plugs and the third mesh piece are necessary. Therefore, the first kit contains first plug 10, second plug 20, and third mesh piece 40. A second kit is for an indirect inguinal hernia operations on female patients. This kit comprises first plug 10 and second mesh piece 30. This kit does not include the second plug and the third mesh piece because it is not necessary for female patients to have plug 20 or mesh piece 40. Both plug 20 and mesh piece 40 have holes 22 and 50 respectively that are cut out for spermatic cords that are not present in females.

During surgery, a surgeon can open a kit to apply these precut sterilized plugs into an inguinal box in a patient, thereby avoiding the steps of cutting and sterilizing each plug during hernia surgery. During an operation on a male patient, a surgeon has the option to insert either first plug 10 or second plug 20 within a patient's body.

Figure 2A:
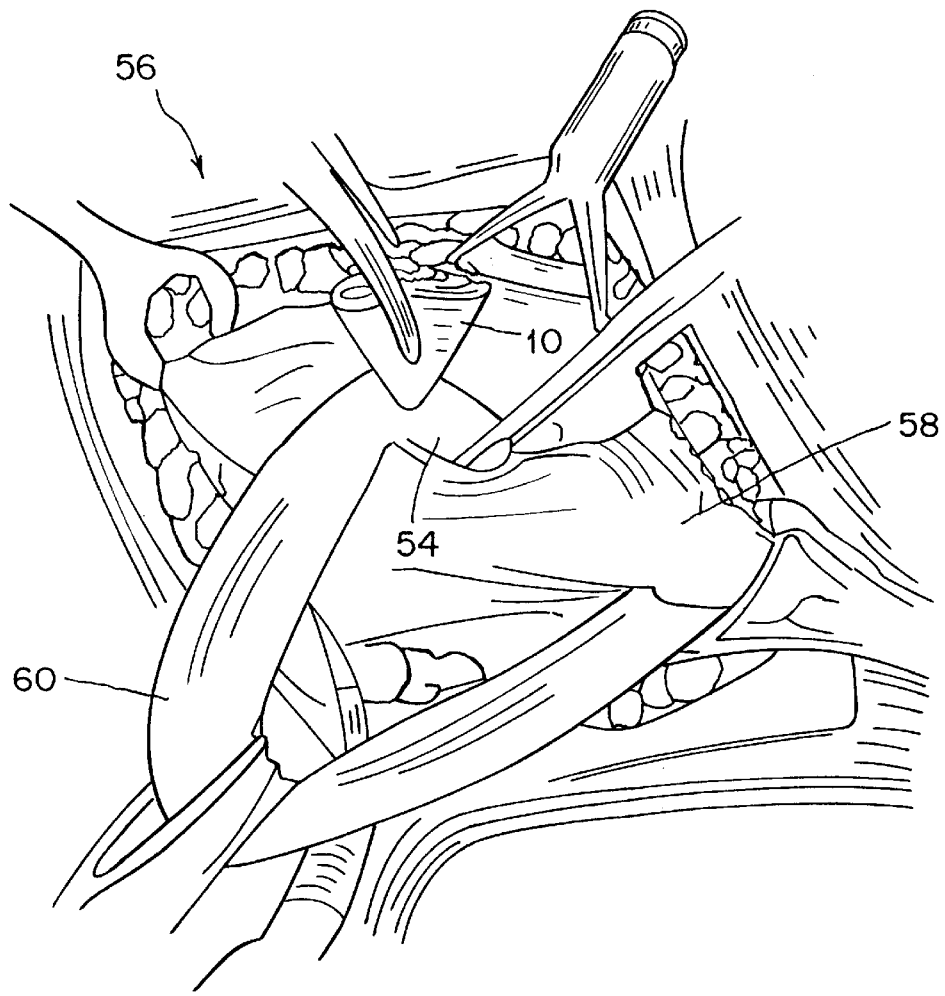
FIG. 2A shows the hernial plug of FIG. 1A inserted into an opening in the body near the spermatic cord.

For example, FIG. 2A shows pinched plug 10 as shown in FIG. 1B being inserted into the body of a patient during hernia surgery. During surgery, an inguinal box is exposed which forms a superficial inguinal ring 56. Pinched plug 10 fits within an enlarged deep inguinal ring 54, after cutting through transversalis fascia 58 which forms the bottom layer of superficial inguinal ring 56.

Figure 2B:
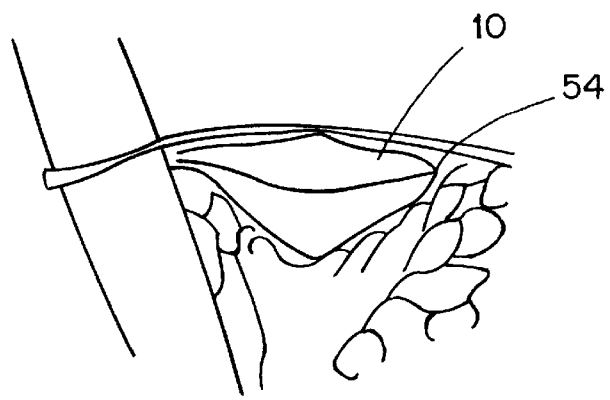
FIG. 2B shows the plug in FIG. 1A inserted into the body.

FIG. 2B shows plug 10 inserted into the body and positioned inside inguinal ring 54. Plug 10 fits near spermatic cord 60 inside the body.

Figure 3A:
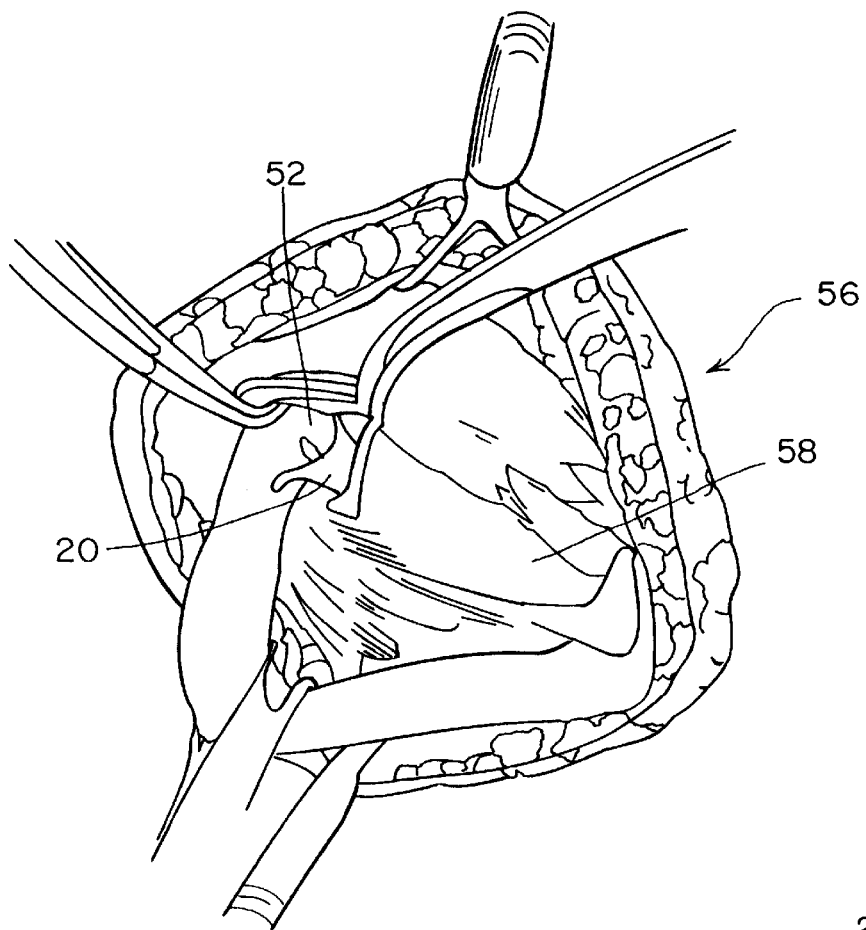
FIG. 3A shows the opening for inserting the hernial plug.

FIG. 3A shows the second option for the operation wherein a surgeon can instead insert plug 20 into deep inguinal ring 54. Plug 20 fits inside deep inguinal ring 54 to cover the hernia sac. In this case, it is positioned inside inguinal ring 54 and under transversalis fascia 58.

Figure 3B:
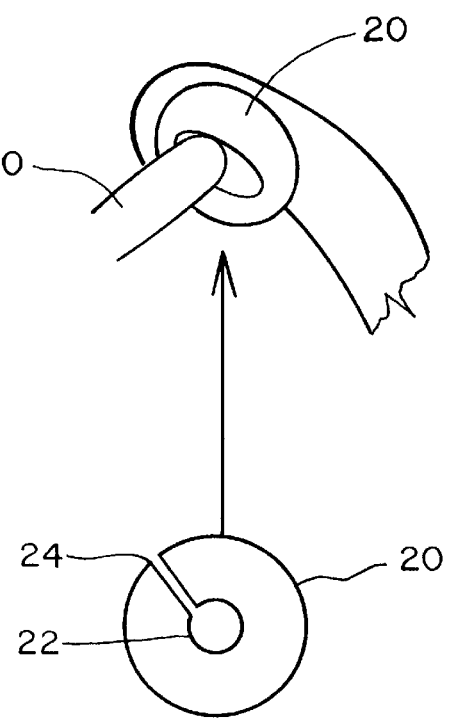
FIG. 3B shows the hernial plug of FIG. 1C fitting around the spermatic cord.

FIG. 3B shows plug 20 fitted around spermatic cord 60. With this design, plug 20 is less likely than plug 10 to slip or move within the body because plug 20 fits snugly around spermatic cord 60. In this case, slit 24 opens up plug 20 so that with hole 22 it can fit around the cord 60. Since this new plug is a flat plug, it does not compress the iliac vein after it is inserted into the body.

Figure 4:
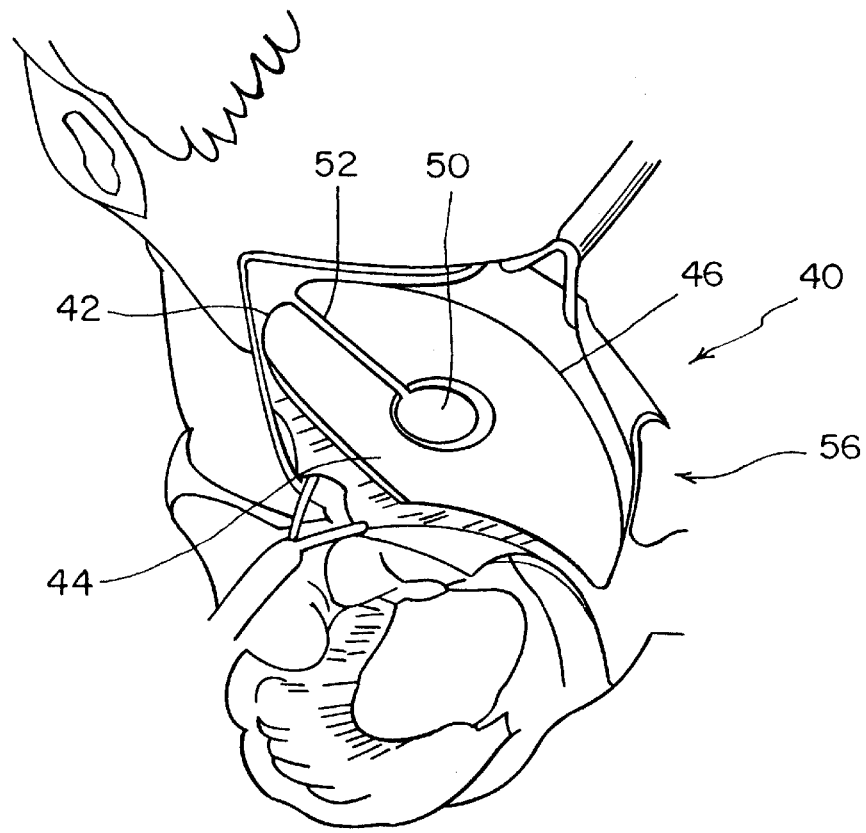
FIG. 4 shows the hernial plug of FIG. 1D fitting inside the body.

The next step in the operation is shown in FIG. 4. FIG. 4 shows mesh piece 40 as it fits inside the body. Mesh piece 40 contains hole 50 and slit 52 which allows it to open up along edge 42 to allow mesh piece 40 to fit around spermatic cord 60. Mesh piece 40 fits inside the superficial inguinal ring 56, over transversalis fascia 58 and over deep inguinal ring 54 housing either plug 10 or 20.

A similar kit can be used when operating on a female patient. However, a female patient does not have spermatic cord 60 so plug 20 and mesh piece 30 are not needed in this kit. For example, the kit for a female patient includes plug 10 and hernia mesh piece 30. In this operation, plug 10 is inserted into deep inguinal ring 54, underneath transversalis fascia 58. Next, mesh piece 30 is placed into superficial inguinal ring 56 over transversalis fascia 58 and plug 10.

Figure 5:
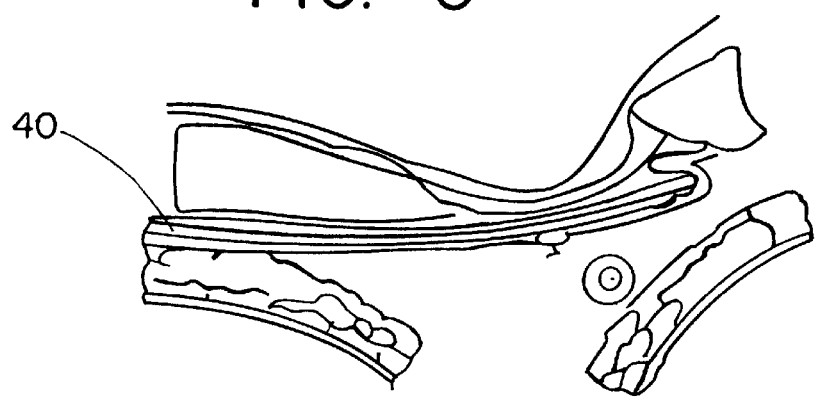
FIG. 5 shows a cross-sectional view of a hernial plug as it fits inside the body.
Figure 6:
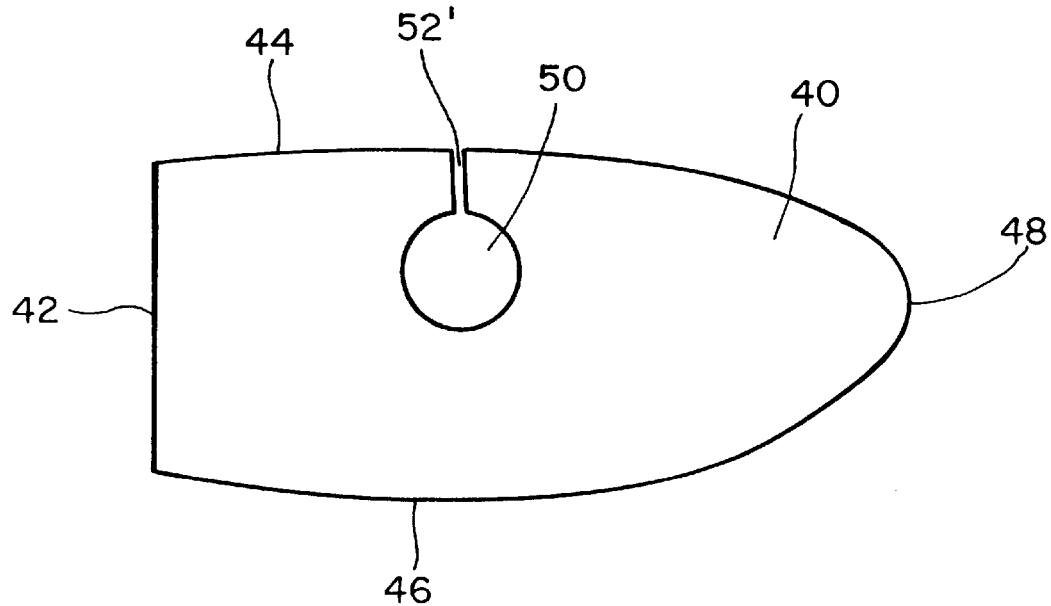
Figure 7:
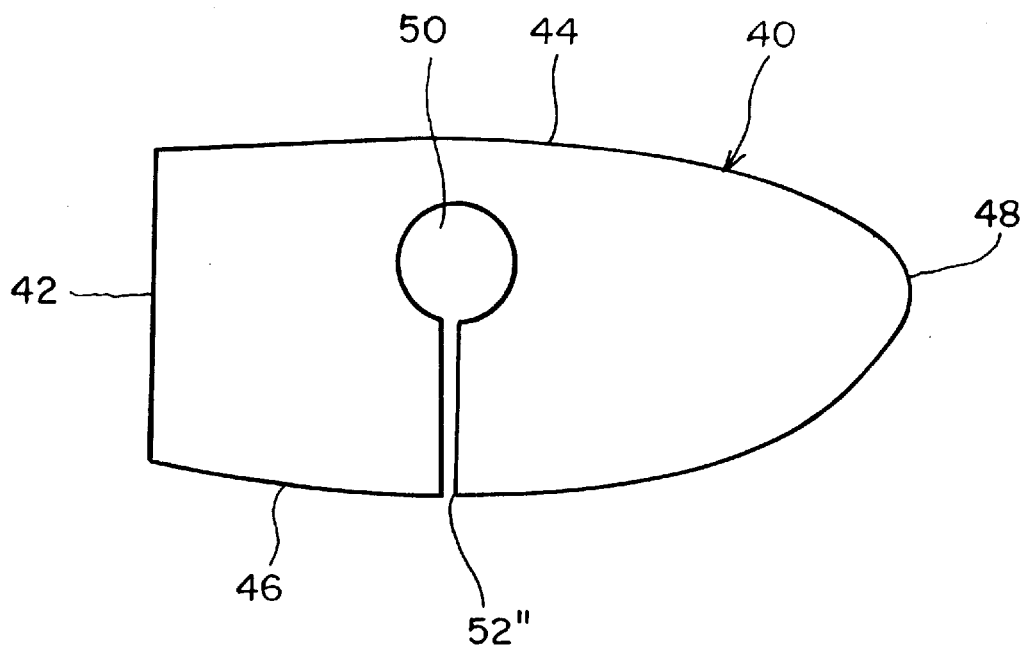

FIG. 5 shows mesh 40 as it fits inside the body. Mesh piece 40 is designed to lay flat within the body so that there is no overlap or bunching. This feature is important because if a plug a mesh piece becomes deformed or moves within the body then there could be the development of seromas, deformities, and incomplete fibrous infiltration. Both mesh piece 40 and mesh piece 30 lay flat within the body because they were made from a stiff polypropylene mesh that was pre treated to diminish memory in the piece. Finally these mesh pieces do not have to be sutured or stapled within the body because they are positioned within the inguinal box.

Accordingly, while only two embodiments of the present invention have been shown and described, it is to be understood that many changes and modifications may be made thereunto without departing from the spirit and scope of the invention as defined in the appended claims.

What is claimed is:

1. A substantially flat hernia plug and mesh kit comprising:
   a substantially flat first mesh plug that has a circular shape;
   a substantially flat second circular mesh plug having a hole cut substantially in a center region of the plug, and a slit cut in one end of said plug leading to the hole; and
   a first mesh piece that is tear drop-shaped having a center hold cut within the plug and a slit cut into the plug, the slit extending from an edge of the plug to the hole, said plug having a flat right edge, a rounded left edge a rounded top edge and a rounded bottom edge, wherein said first mesh plug, said second mesh plug, and said first mesh piece are designed to fit secure inside a patient without staples or sutures.

2. The kit as claimed in claim 1, wherein said first plug has a diameter of at least 2.5 centimeters.

3. The kit as claimed in claim 1, wherein said first plug has a diameter of at least 4.5 centimeters.

4. The kit as claimed in claim 1, wherein said second mesh plug has a diameter of at least 2.5 centimeters.

5. The kit as claimed in claim 1, wherein said second mesh plug has a diameter of at least 4 centimeters.

6. The kit as claimed in claim 1, wherein said first mesh piece has a length of at least 9 centimeters.

7. The kit as claimed in claim 1, wherein said first mesh piece has a width of at least 3.5 centimeters.

8. The kit as claimed in claim 1, wherein a center of said hole on said mesh piece is positioned 3 centimeters from said top edge and 1.5 centimeters from said bottom edge.

9. The kit as claimed in claim 1, wherein on said mesh piece has a length of at least 10 centimeters from said right edge to said left edge.

10. The kit as claimed in claim 1, wherein the width of said mesh piece is at most 4.5 centimeters.

11. A hernia kit comprising:
    a substantially flat mesh plug that has a circular shape; and
    a mesh piece that is tear drop-shaped said mesh piece having a substantially flat right edge, a rounded left edge, a rounded top edge and a rounded bottom edge wherein when a inguinal box is exposed on a person a surgeon can open this kit and place said mesh plug into said person, mesh piece into a person so that said mesh piece covers said hernia.

12. The kit as claimed in claim 9, wherein said mesh piece has a length of at least 10 centimeters from said right edge to said left edge.

13. The kit as claimed in claim 9, wherein said mesh piece has a width of 4.5 centimeters at its widest point.

14. The kit as claimed in claim 9, wherein said right edge of said mesh piece is at least 4 centimeters long.

* * * * *